United States Patent [19]

Tyo

[11] 4,296,761
[45] Oct. 27, 1981

[54] CONVERTIBLE PARAPODIUM

[75] Inventor: James H. Tyo, Jackson, Mich.

[73] Assignee: Camp International, Inc., Jackson, Mich.

[21] Appl. No.: 143,608

[22] Filed: Apr. 25, 1980

[51] Int. Cl.³ .............................................. A61F 3/00
[52] U.S. Cl. .................................................. 128/80 G
[58] Field of Search ................ 128/80 R, 80 F, 80 G, 128/83, 87 R, 88; 297/39, 384, DIG. 10

[56] References Cited

U.S. PATENT DOCUMENTS

| | | | |
|---|---|---|---|
| 2,573,866 | 11/1951 | Murphy | 128/80 F |
| 2,772,674 | 12/1956 | Swiech | 128/80 F |
| 3,423,773 | 1/1969 | Yamate | 5/68 |
| 3,750,659 | 8/1973 | Loomans | 128/80 R |
| 4,029,089 | 6/1977 | Mulholland | 128/80 R |

Primary Examiner—John D. Yasko
Attorney, Agent, or Firm—Beaman & Beaman

[57] ABSTRACT

A parapodium for use by patients having paralysis of the lower extremities, cerebral palsy, or the like, usually children, which permits the user to stand in an upright manner, and is convertible to a seated position. The convertible parapodium supplies body support in either the upright or seated position, and includes a base receiving the user's feet from which lateral columns arise and support pivot plates to which parallelogram linkages are attached. The parallelogram linkages support seat and back structure and legs attached to the back structure engage the floor when the device is converted to a seat configuration.

7 Claims, 6 Drawing Figures

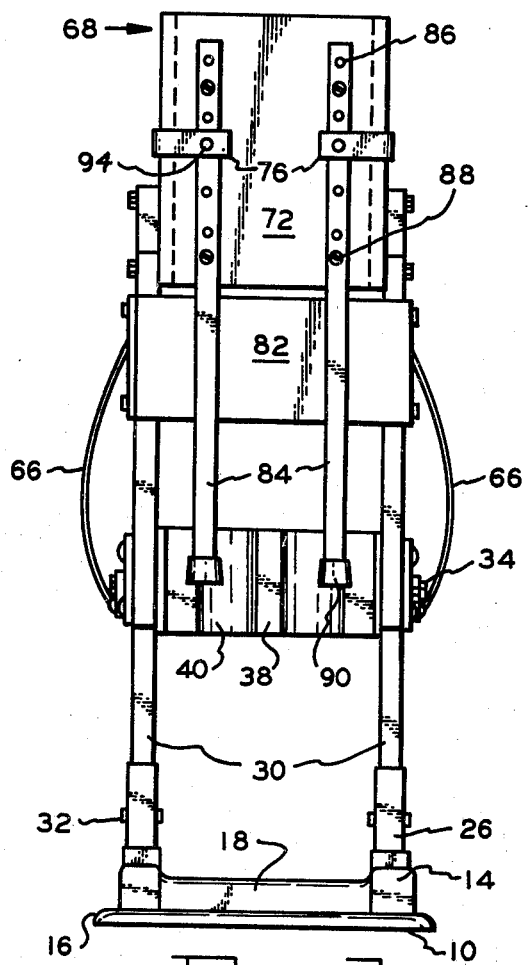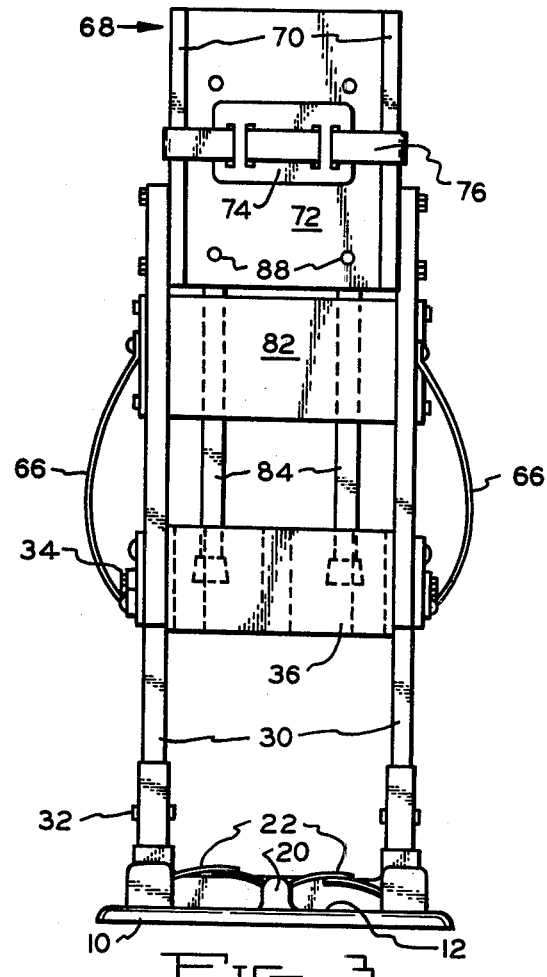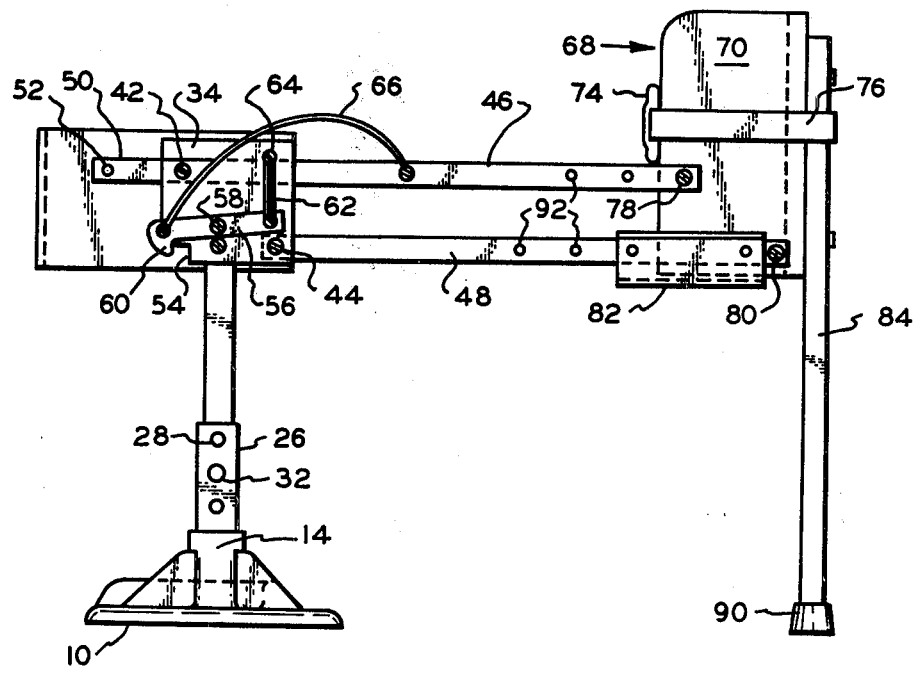

CONVERTIBLE PARAPODIUM

BACKGROUND OF THE INVENTION

Parapodiums, also known as ambulation and mobility platforms, are used with victims of lower paralysis, cerebral palsy, and similar diseases and medical problems, particularly with children, wherein the patient is unable to stand unaided. Such patients require significant firm support in either a standing or sitting position, but if adequately supported are able to function well with the arms and hands, and in many cases, become ambulatory by the use of crutches. It is important that such patients spend time each day standing to prevent bone and muscle structure in the legs and hips from softening. Additionally, the use of a parapodium is important from the psychological aspect of permitting the child to participate, within limits, in group activites, and for the child to be ambulatory with the use of crutches reduces the supervision and care required.

Leg bracing devices as shown in U.S. Pat. Nos. 2,573,866 and 2,772,674 provide the type of aid which permits patients having paralysis in the lower extremities, to stand and maneuver with crutches. Likewise, the orthopedic device shown in U.S. Pat. No. 3,423,773 permits smaller children to be supported in a safe manner in a substantially upright position. Crutchless standing devices providing the necessary support to permit patients to remain, unaided, in an upright position are shown in U.S. Pat. Nos. 3,750,659 and 4,029,089, and these devices have contributed toward the rehabilitation of paralysis, cerebral palsy and nervous disorder patients. However, prior art devices are usually of such bulk and complexity as to be difficult to use by children, expensive, and usually limited to supporting the patient in an upright, or substantially upright, position.

It is an object of the invention to provide a convertible parapodium orthopedic device especially suitable for use by children which permits crutchless standing in an upright position, or may be easily converted to support the child in a seated position.

An additional object of the invention is to provide a convertible parapodium which is of economical manufacture, relatively concise in configuration, easily transported, may be readily used by the unskilled, and is easily cleaned and maintained.

Yet another object of the invention is to provide a convertible parapodium which may be readily adjusted to the size of the user, which permits the patient to be easily placed therein or removed therefrom, and wherein orientation between leg and back supporting portions of the parapodium are maintained at a predetermined angular relationship in both the standing and seating adjusted positions to insure adequate support of the body portions in both operating modes of the device.

An additional object of the invention is to provide a parapodium convertible between standing and seated modes wherein locking means prevent accidental operation of the device between its operating modes, and yet, the device is readily converted between standing and seated conditions by the unskilled and without hardware modification.

In the practice of the invention the convertible parapodium includes a base upon which the patient's feet are supported. Columns are affixed to lateral portions of the base and arise therefrom each having a pivot plate attached to their upper end having leg bracing means extending therebetween. The pivot plates also provide the support for a pair of parallelogram linkages, and latching structure is mounted upon the pivot plates controlling pivoting of the parallelogram linkages between standing and seated conditions.

Back supporting means are pivotally attached to the other end of the parallelogram linkages, and the linkages also constitute the support for seat structure. The seat structure will be disposed at the rear of the patient's legs during the standing mode, and is located below the patient's hips when the parallelogram linkage is pivoted to the seated mode.

The parallelogram support of the back supporting means maintains the back support parallel of the columns in both the standing and seated modes, and patient confining means in the form of a chest pad is mounted upon the back support extending across the patient's chest. Legs affixed to the back support extend in a downward direction having a lower end engaging the floor when the parapodium is in the seated mode.

The latches mounted upon the pivot plates hold the parallelogram linkage in the upright condition, and when it is desired to use the parapodium in the seated mode the latches are operated to permit the desired pivoting of the linkages. The parapodium structure is relatively open and accessible for cleaning and maintenance, and the structural components are of such configuration and fabrication as to be economically manufactured.

BRIEF DESCRIPTION OF THE DRAWINGS

The aforementioned objects and advantages of the invention will be appreciated from the following description and accompanying drawings wherein:

FIG. 2 is a rear, elevational view of the parapodium of FIG. 1, FIG. 3 is a front, elevational view of the parapodium in accord with the invention, FIG. 5 is a side, elevational view of FIG. 4 illustrating the parapodium in the seated position.

DESCRIPTION OF THE PREFERRED EMBODIMENT

Figure 1:
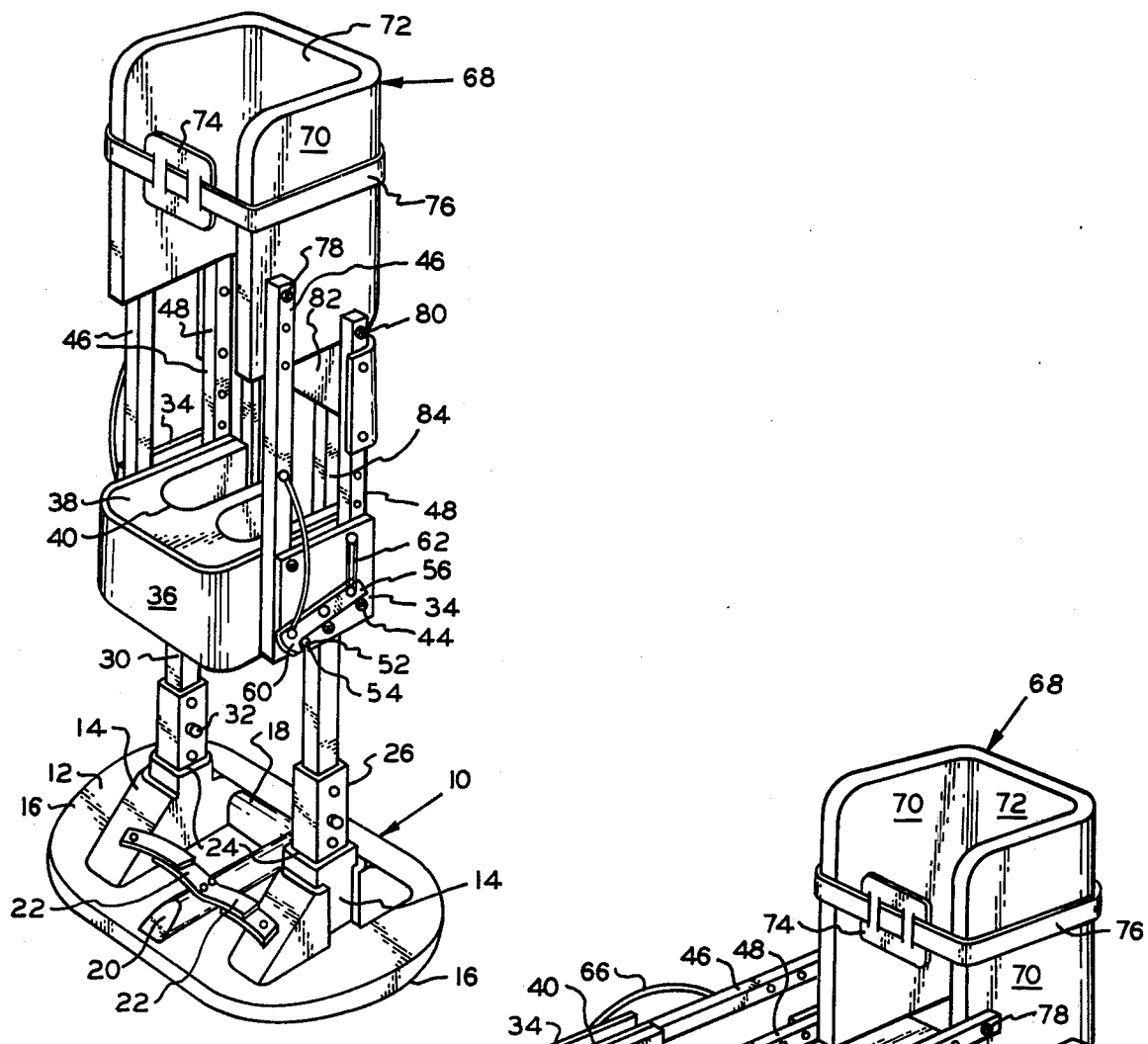
FIG. 1 is a perspective view taken from the front and left side of a convertible parapodium in accord with the invention when in the standing position.

The parapodium is supported upon a base 10 which is preferably formed of a molded synthetic plastic and includes an upper surface 12 having homogeneous embossments arising therefrom. These embossments include column supporting portions 14 disposed adjacent the base lateral sides 16, and the embossment 18 extending between portions 14 includes a median 20 which defines foot receiving wells on the surface 12, and the embossment 18 will serve to locate the patient's heel and foot straps 22 mounted on embossments 14 and 20 position the feet within the wells. Preferably, the periphery of the base 10 is rounded at its lateral sides 16 which aids in maneuvering the parapodium, particularly when the wearer is employing crutches for ambulatory purposes.

The portions 14 each include a rectangular opening 24 into which a metallic adjustment tube 26 is affixed, either by molding or adhesive. A tube 26 includes a plurality of axially spaced holes 28, and each tube receives a rectangular column 30 axially positioned within the associated tube. The column 30 may be fixed with respect to its associated tube 26 by means of a bolt or pin 32 extending through the tube holes 28, and a hole, not shown, in the associated column.

A pivot plate 34 is affixed to the upper end of each column 30, and a leg brace 36 of a U configuration is affixed to the inside surfaces of the pivot plates 34 interconnecting the plates and imparting rigidity to the columns. A leg receiving cushion 38, preferably formed of a soft foam or other resilient material, is mounted to the inside of the leg brace 36 and includes leg receiving recesses 40 which receive the patient's legs, usually in the vicinity of the knee.

Each pivot plate 34 includes a pair of linkage pivots 42 and 44 upon which the links 46 and 48 of a parallelogram linkage are pivotally mounted. The upper link 46 includes an extension 50 projecting beyond its pivot 42, and this extension includes a stud 52 adapted to be received within a notch 54 defined in the lower edge of the associated pivot plate 34 when the linkage is pivoted to the standing or upright position as shown in FIG. 1.

In order to maintain the linkage in the standing position a latch lever 56 is pivotally mounted upon each pivot plate upon a pivot 58, and each latch lever includes a hook 60 which overlaps and locks the associated stud 52 within notch 54, as will be appreciated from FIG. 1. A spring 62 affixed to the end of the lever 56 and an anchor 64 formed on the associated pivot plate bias the latch lever in a direction to force the hook downwardly trapping the stud within the notch. The spring 62 preferably consists of a rubberband, which may be easily replaced, but may take the form of a conventional tension coil spring. An operating lanyard 66 may be affixed to one end to the hook end of the latch lever, and attached at the latch.

The upper or outer end of the links 46 and 48 are pivotally connected to back supporting means 68. The back supporting means is in the form of a U shaped member having lateral side pieces 70 extending parallel to the plane of the associated linkages interconnected by a base portion 72 adapted to engage the back of the patient. The member 68 is preferably formed of a relatively rigid, but cushioned, member, and may be synthetic plastic or foam, or may constitute a metal component which is upholstered or otherwise cushioned. Preferably, a chest pad 74 is affixed to the back supporting member 68 by adjustable straps 76 affixed to the member at the rear.

Figure 4:
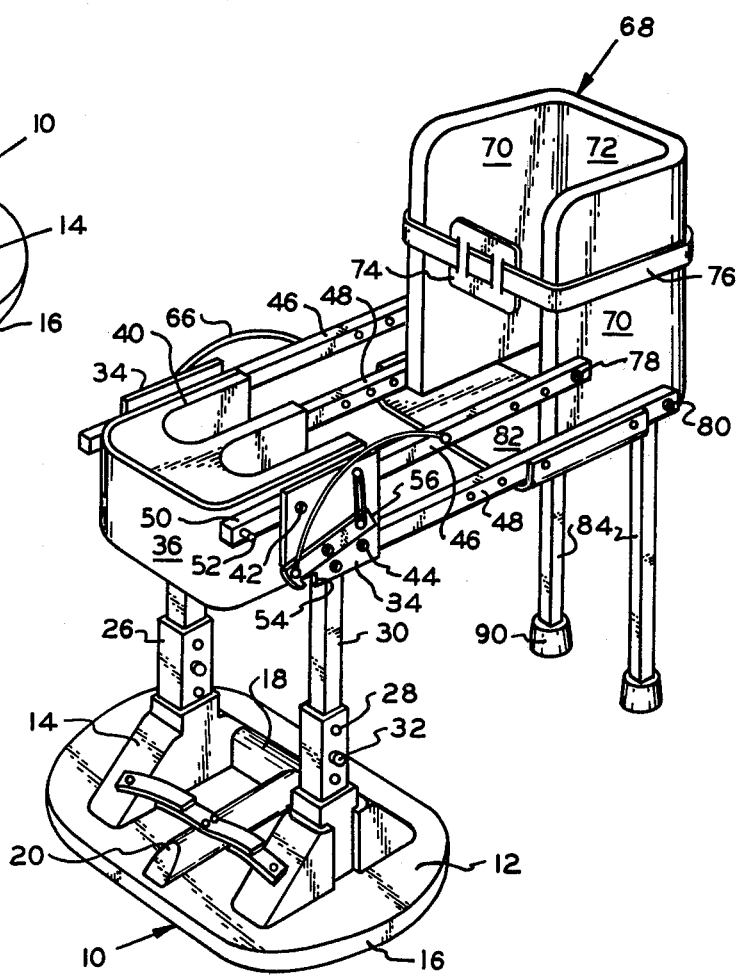
FIG. 4 is a perspective view as taken from the front and left side of the convertible parapodium illustrating the device in the seated mode.

The pivots 78 and 80 pivotally attach the links 46 and 48, respectively, to the back supporting sides 70, and as the location of the pivots 78 and 80 relative to each other corresponds to the angular relationship between pivots 42 and 44 the links constitute a true parallelogram whereby the plane of the member base portion 72 will always be vertical regardless of whether the convertible parapodium is in the standing or sitting mode. For sitting purposes, a seat band 82 is affixed under the links 48 adjacent the pivot pins 80, FIG. 4, and the width of the seat 82 in the direction of the length of the links is sufficient to comfortably support the patient.

The upper region of the parapodium is supported, when in the seated mode, by a pair of legs 84 affixed to the outer surface of the back supporting member base 72. The legs 84 are formed of square tubing and are provided with a plurality of axially spaced holes 86 for permitting adjustable mounting of the legs upon the back member base by screws 88, and the lower end of the legs include tubber tips or cane ends 90 for cushioning engagement with the floor. At all times the legs 84 extend in a direction parallel with the plane of the back member base portion 72. The straps 76 are attached to the legs 84 by snap fasteners 94.

The convertible parapodium in accord with the invention is readily adjustable, within limits, to accommodate various size patients, or growth. This adjustment is achieved by the plurality of holes 28 within the tubing 26, the holes 86 within the legs 84, and the plurality of holes 92 defined within the links 46 and 48 which selectively receive the pivots 78 and 80 wherein the distance between the pivot plates 34 and back supporting member 68 may be adjusted.

In use, assuming the apparatus has been previously adjusted to the desired size, the child is placed within the parapodium, either in the upright or sitting position, by releasing the chest pad straps 76, placing the child within the back member side pieces 70 and the feet upon the base surface 12 on each side of median embossment 20 under foot straps 22. Upon the chest pad 74 being located upon the wearer's chest, and positioned by straps 76 by affixing the straps to the legs 84 by snap fasteners 94 the parapodium may now be used in either the standing position as shown in FIGS. 1-3, or in the sitting position shown in FIGS. 4 and 5. The presence of the parallelogram linkages produces a strong interconnection between the leg bracing plate 36, seat 82 and back supporting member 68. The child may be placed in, and removed from, the parapodium easily, and with the device in the upright position as shown in FIG. 1 children having upper mobility may utilize crutches to become ambulatory.

It is appreciated that various modifications to the invention concepts may be apparent to those skilled in the art without departing from the spirit and scope of the invention.

I claim:

1. A parapodium for permitting crutchless standing and convertible to a seat without structural modification comprising, in combination, a base having a standing surface defined thereon and including lateral sides, a column mounted adjacent each base lateral side extending upwardly from said base each having an upper end, a pivot plate mounted upon each column upper end, a pair of parallelogram linkages each having a first end pivotally mounted upon a pivot plate and a second end each pivotally affixed to a back supporting member, horizontal leg bracing means extending between said pivot plates, a seat affixed to said linkages adjacent said back supporting member, elongated leg means supported by said back supporting member, and linkage locking means defined upon said pivot plates selectively engaging and releasing said linkages permitting said linkages to be pivoted from a vertical standing position wherein said seat is substantially vertically oriented and said leg means are in a raised position above said base to a substantially horizontal sitting position wherein said seat is substantially horizontally oriented and said leg means are in a lowered ground supported position offset with respect to said base.

2. In a parapodium as in claim 1 wherein said linkage locking means includes a latch pin fixed with respect to its associated linkage, and a pivotal lever selectively cooperating with said latch pin pivotally mounted on the adjacent pivot plate.

3. In a parapodium as in claim 1, said base comprising a synthetic plastic molded body including an upper surface defining said standing surface, and foot orienting bosses defined on said upper surface adjacent said standing surface.

4. In a parapodium as in claim 1, adjustable column supporting means mounting said columns upon said base for selected vertical adjustment thereto.

5. In a parapodium as in claim 1, wherein said back supporting member is of a U configuration having a base portion and leg portions extending from said base portion having pivots mounted thereon supporting said linkages' second ends.

6. In a parapodium as in claim 5, said leg means comprising a pair of spaced elongated vertical columns each having an upper region adjustable affixed to said back supporting member, said leg columns each including a lower region extending below said back supporting member terminating in a ground engaging end.

7. In a parapodium as in claim 6, a chest pad adjustably mounted upon said back supporting member adapted to extend about the user's chest.

* * * * *